United States Patent [19]

Magovern

[11] Patent Number: 4,791,911
[45] Date of Patent: Dec. 20, 1988

[54] METHOD OF CARDIAC RECONSTRUCTIVE SURGERY

[75] Inventor: George J. Magovern, Pittsburgh, Pa.
[73] Assignee: Allegheny-Singer Research Institute, Pittsburgh, Pa.
[21] Appl. No.: 869,240
[22] Filed: Jun. 2, 1986
[51] Int. Cl.⁴ ............................................ A61B 19/00
[52] U.S. Cl. ............................. 600/36; 128/DIG. 3; 623/3
[58] Field of Search ............... 128/1 D, 419 P, 419 R, 128/DIG. 3; 623/3, 12, 14

[56] References Cited

U.S. PATENT DOCUMENTS

| | | | |
|---|---|---|---|
| 4,411,268 | 10/1983 | Cox | 128/421 |
| 4,662,382 | 5/1977 | Sluetz et al. | 128/419 P |
| 4,666,443 | 5/1987 | Portner | 128/DIG. 3 |

OTHER PUBLICATIONS

Lancet; title, "Myocardial Substitution . . ."; author, A. Carpentier; pp. 1267; date; Jun. 1985.
Journal of Cardiovascular Surgery; title, "Experimental Cardioplasty . . . ", author, J. Schachques; pp. 457–462; date; Sep./Oct. 1985.
Journal of Thoracic Cardiovascular Surgery; title, "Replacement of Ventricular Myocardium . . . "; author, K. J. Macovia; pp. 519-527; date: Apr. 1981.

Primary Examiner—Max Hindenburg
Attorney, Agent, or Firm—Webb, Burden, Ziesenheim & Webb

[57] ABSTRACT

A surgical method of reconstructing damaged cardiac muscle via latissimus dorsi autograft. The latissimus dorsi is dissected from its origin and insertion while maintaining the neurovascular bundle intact. The dissected muscle flap is passed into the thorax through a rib resection in the corresponding axilla. After appropriate midsternotomy, cardiopulmonary bypass, etc., the muscle flap and its preserved neurovascular bundle may be used as graft muscle in the reconstruction of cardiac muscle. The latissimus dorsi autograft minimizes or eliminates the problems of histoincompatibility associated with cardiac transplantation. A subsequent protocol of suitable pacing of the autograft enables it to contribute to the overall cardiac function, and the structural presence of the grafted muscle tissue permits cardiac muscle repair without distorting the shape of the heart in the area(s) of excised cardiac muscle.

7 Claims, 1 Drawing Sheet

METHOD OF CARDIAC RECONSTRUCTIVE SURGERY

FIELD OF THE INVENTION

The present invention relates to surgical alternatives to cardiac transplantation for the repair of ventricular tumor, ventricular aneurism or other localized cardiac damage or disease.

BACKGROUND OF THE INVENTION

Clinical deterioration in cardiac patients results from many known conditions and diseases, including tumors and/or aneurisms, stenosis or other disease of the valves, muscle damage due to myocardial infarction, and the like. Extensive efforts in the area of cardiac transplantation have been undertaken, to combat such cardiac deterioration, in those cases for which alternative treatments proved ineffective.

Notably, progressive cardiac deterioration frequently results from localized cardiac muscle damage which, at least in theory, would not require cardiac transplantation were alternate methods of cardiac reconstruction available. Just as prostheses were developed to repair damaged or diseased cardiac valves, therefore, a significant need persists for a method of reconstructing cardiac muscle in the event of localized damage such as ventricular tumor, aneurism, or other localized abnormality.

BRIEF DESCRIPTION OF THE INVENTION

In order to meet this need, the present invention is a surgical method of reconstructing damaged cardiac muscle via latissimus dorsi autograft. The latissimus dorsi is dissected from its origin and insertion while maintaining the neurvascular bundle intact. The dissected muscle flap is passed into the thorax through a rib resection in the corresponding axilla. After appropriate midsternotomy, cardiopulmonary bypass, etc., the muscle flap and its preserved neurovascular bundle may be used as a graft muscle in the reconstruction of cardiac muscle. The latissimus dorsi autograft minimizes or eliminates the problems of histoincompatibility associated with cardiac transplantation. A subsequent protocol of suitable pacing of the autograft enables it to contribute to the overall cardiac function, and the structural presence of the grafted muscle tissue permits cardiac muscle repair without distorting the shape of the heart in the area(s) of excised cardiac muscle.

DETAILED DESCRIPTION OF THE INVENTION

Figure 1:
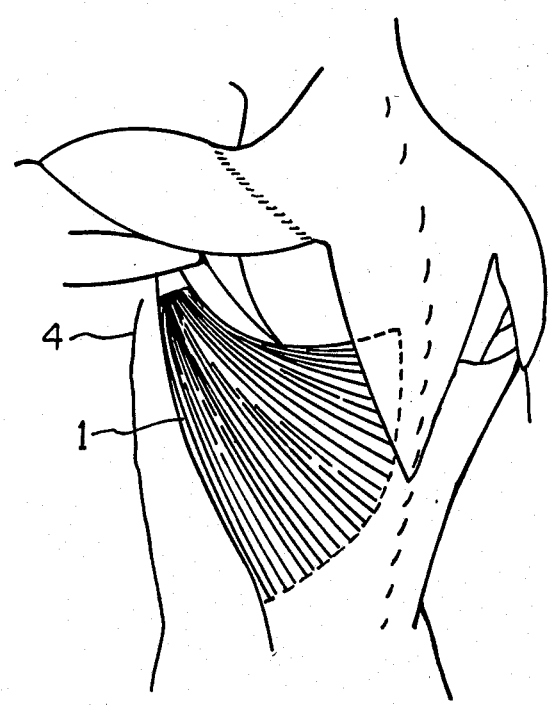
FIG. 1 is a perspective view of the left dorsal thorax of the human body, showing in cutaway the subcutaneous latissimus dorsi 1.
Figure 2:
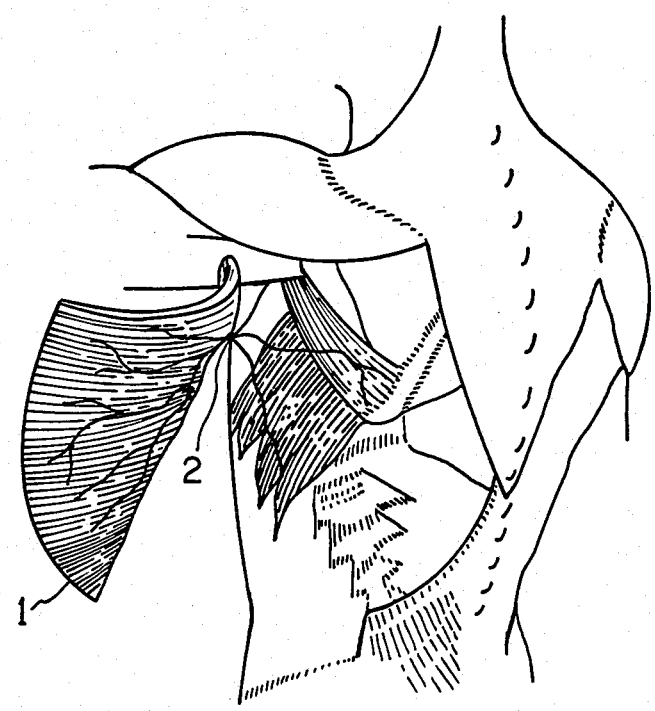
FIG. 2 is a perspective view of the left dorsal thorax of the human body subsequent to the dissection of the latissimus dorsi 1 but with preservation of the neurovascular bundle 2.
Figure 3:
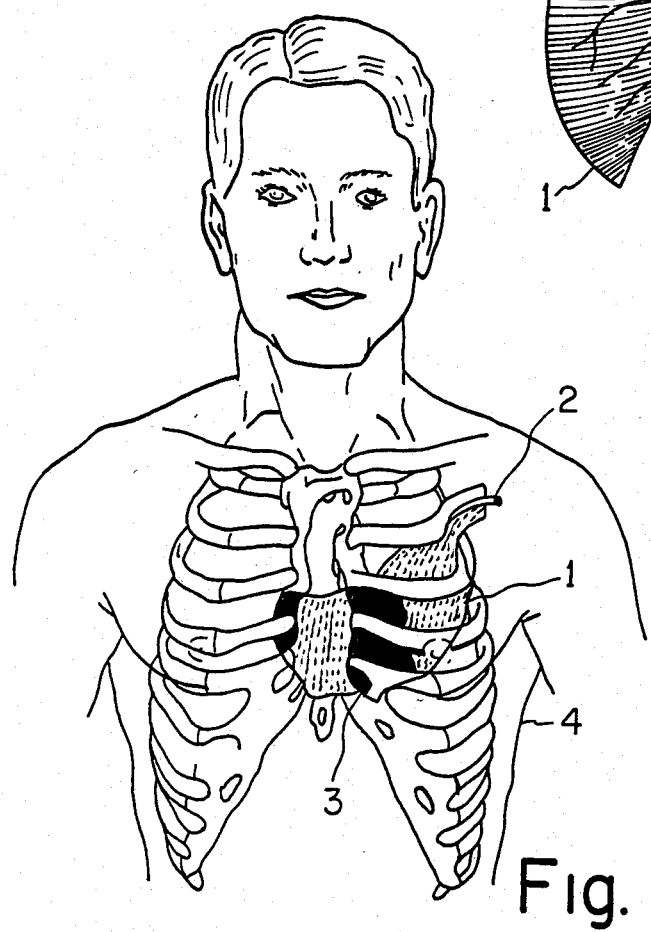
FIG. 3 is a perspective view of the ventral thorax of the human body showing the dissected latissimus dorsi in position as a cardiac autograft.

Referring now to FIG. 3, the latissimus dorsi autograft 1 is shown in place and wrapped around the heart 3 to which it is sutured. Although truncated for the purposes of illustration, the neurovascular bundle 2 maintains the same neurovascular interconnections it has prior to the cardiac reconstruction procedure. As described in greater detail below, the autograft is a reconstruction of a ventricular aneurism and is held in place in combination with a bed of fibrous endocardial tissue. FIGS. 1 and 2 illustrate the position and dissection, respectively, of the latissimus dorsi prior to the autograft.

The surgical implementation of the above-summarized surgical cardiac autograft is best described in the context of an actual case history.

Angiographic studies of a patient, who had suffered previous myocardial infarctions, showed diffuse coronary disease and a large antero-apical calcified ventricular aneurism. Muga ejection fraction was 30 percent. The present method of cardiac reconstructive surgery was selected as the appropriate reparative procedure.

The patient underwent routing postoperative preparation and anesthesia. Through a separate flank incision (see FIG. 1) the left latissimus dorsi 1 was dissected from both its origin and insertion while at the same time the surgeon carefully maintained the neurovascular bundle 2 and its associated neurovascular structures. A segment (approximately 3–4 cm. square) of the second rib was resected in the axilla 4. The latissimus dorsi 1 and neurovascular bundle 2 were passed through the resection and into the thoracic cavity (left hemithorax). To maximize anatomic stability of the autograft, the origin of the latissimus dorsi was fixed to the third rib. The flank incision was sutured and the patient was rolled from the side to his back.

By means of a midsternotomy, cardiopulmonary bypass, hypothermia, and cardioplegia (and the associated cardiovascular surgical techniques associated with such procedures) the large antero-apical calcified ventricular aneurism was excised. The scarred endocardium and a small rim of the aneurism was dissected free to allow for flap closure, which was achieved with interrupted 3-0 pledgeted tycron sutures. An area approximately 6 cm. in length by 4 cm. in width of fibrous endocardial tissue provided a bed for the latissimus dorsi, which was fixed to the edges of the fibrous closure and over the surface of the left and right ventricles.

For sensing and stimulation of the muscle flap a bipolar A-V sequential symbiosis pacer was applied to the right atrium. Two epicardial type screwon type leads associated with the atrial pacer were placed on the latissimus dorsi, with the first near the neurovascular bundle and the second over the muscle as it lay on the repair. All incisions were closed and postoperative care effected. On the eighth postoperative day, muscle pacing was commenced at 2.5 MV for 150 milliseconds for four hours twice a day. This was gradually increased over a three week period to 5 MV and 200 watt seconds, continuous pacing, with the muscle pacer R-wave adjusted to be synchronous with the QRS of the patient's cardiogram. The patient was discharged from the hospital approximately one month after surgery.

In the sixth postoperative week, the muscle flap and heart were examined. With the pacer off, a definite decreased contraction of the anterior left ventricular wall could be observed, accompanied by an increased pulse rate. With synchronous pacing (i.e., muscle pacer R-wave synchronous with patient's QRS) the heart rate slowed and the muga ejection fraction increased approximately 5 percent to 51 percent. The improvement was encouraging particularly because optimal physiological muscle changes (gradual conversion to fast and slow twitch oxidative fatigue-resistant fibers) had not been expected prior to three of four months after the commencement of pacing stimulation.

Based on the above case history, a general method of cardiac reconstructive surgery can be derived. The surgical method is suitable for use in patients suffering localized cardiac muscle damage or disease when such damage or disease requires excision. The latissimus dorsi autograft permits such excision and repair of the affected cardiac muscle by providing a replacement for the damaged or diseased tissue. The autograft (1) provides histocompatability; (2) remains viable contracting muscle which participates in heart pumping when synchronously paced; and (3) prevents constriction of the affected cardiac chamber, which would occur were the original cardiac muscle merely resutured after the required excision.

As a result of these benefits, the present method of cardiac reconstructive surgery is suitable for cardiac tissue repair under numerous circumstances. As described above the latissimus dorsi autograft may be used to repair the area of calcified aneurism excision from one or both ventricles. The procedure may also be used to repair one or both ventricles after removal of associated tumors. The autograft may even be used to repair limited loci of cardiomyopathy attributable to, for example, myocardial infarction.

The presently disclosed surgical procedure parallels the same basic outline as the specific case history described above. Surgery commences with the patient lying on his or her right side, and the left latissimus dorsi is dissected (with the neurovascular bundle retained intact and attached) and inserted into the left hemithorax via an axillary resection of the second rib. The origin of the latissimus dorsi is secured to the third rib, for structural stability. Flank incisions are closed and the patient is turned onto his or her back. In association with routine cardiac surgery procedures, the latissimus dorsi is placed over and sutured to the necessary portion of the heart (often by means of fibrous endocardial tissue near the affected area) to form an autograft for the reconstruction of tissue excised due to disease or damage. A bipolar A-V sequential symbiosis pacer is applied to the right atrium and two epicardial type screw-on leads associated with the atrial pacer are placed on the autograft, one near the neurovascular bundle and another on the muscle in position over the cardiac repair. The proper conclusory operative and postoperative procedures are executed in accordance with methods known in the art.

When the general condition of the patient permits, practice of the present surgical technique ideally incorporates the preconditioning of the latissimus dorsi prior to the autograft. Pacing stimulation signals are generated having parameters established by the same contraction parameters as will be required to synchronize the R-wave of the pacer with the QRS of the patient, except that the stimulation of the latissimus dorsi is carried out, for several preoperative weeks, while the muscle is still in its original anatomic position. This preoperative conditioning stimulation commences the gradual conversion of the fast-twitch glycolytic fibers into fast and slow twitch oxidative, fatigue-resistant fibers and thus expedites progress in the autograft patient. Postoperative pacing does not begin until several days after surgery, however, to allow the autograft to head before contractions, which might otherwise tear the sutures, begin.

Should a second reconstructive surgery become necessary, the right latissimus dorsi may be used in the above-described procedure. However, for obvious anatomic reasons pertaining to the preservation of the neurovascular bundle, the left latissimus dorsi is preferred.

EXPERIMENTAL EXAMPLE 1

The patient, having a latissimus dorsi autograft in accordance with the specific case history described above, was examined in the sixth postoperative week. The patient underwent a stress test with cardiac output (ejection fraction) measured by echocardiography. With the pacemaker turned on, the patient was able to sustain exercise for seven minutes with an ejection fraction of 40 and an acceptable heart rate in fact. (The preoperative ejection fraction, as stated above, had been only 30.) The surgeon noted that the patient stopped exercising because of leg fatigue and not due to shortness of breath. After a rest period, the patient underwent a second stress test but with the pacemaker turned off. The patient continued exercise for only five minutes, experienced a doubled heart rate, and was forced to stop due to shortness of breath (indicating a lack of oxygen in the blood stream due to the heart's diminished capacity).

Although the invention has been described with reference to particular materials and particular processes, the invention is to be limited only insofar as is set forth in the accompanying claims.

I claim:

1. A method of cardiac reconstructive surgery, comprising the steps of:
    (a) dissecting the latissimus dorsi from its origin and insertion while maintaining the neurovascular bundle intact;
    (b) directing the resultant dissected latissimus dorsi into the left hemithorax;
    (c) grafting at least a portion of said latissimus dorsi to at least one locus of cardiac muscle;
    (d) positioning a pacer onto the right atrium;
    (e) positioning a first epicardial lead near said neurovascular bundle of the latissimus dorsi; and
    (f) positioning a second epicardial lead near said locus;

whereby contraction of the latissimus dorsi and cardiac pacing may be synchronized.

2. In the method according to claim 1, the step further comprises the step of:
    (c) grafting at least a portion of said latissimus dorsi onto at least one locus of cardiac muscle from which tissue has been excised;

3. In the method according to claim 2, the step further comprises the step of:
    (d) positioning a bipolar A-V sequential symbiosis pacer on the right atrium;.

4. In the method according to claim 3, the step further comprises the step of:
    (b) directing the resultant dissected latissimus dorsi into the left hemithorax and affixing the origin of said latissimus dorsi to the third rib;.

5. In the method according to claim 4, the step further comprises the step of:
    (c) grafting at least a portion of said latissimus dorsi to at least one locus of cardiac muscle, from which tissue has been excised, while maintaining the original shape of the cardiac chamber adjacent said locus of cardiac muscle;.

6. In the method according to claim 5, the step further comprises the step of:
   (b) directing the resultant dissected latissimus dorsi into the left hemithorax via resection of a rib;.

7. A method of cardiac reconstructive surgery, comprising the steps of:
   (a) preconditioning the latissimus dorsi in its normal anatomic position on the human body;
   (b) surgically dissecting said latissimus dorsi from its origin and insertion while maintaining the neurovascular bundle intact;
   (c) directing the resultant dissected latissimus dorsi into the left hemithorax via resection of a rib;
   (d) grafting at least a portion of said latissimus dorsi to at least one locus of cardiac muscle;
   (e) positioning a bipolar A-V sequential symbiosis pacer on the right atrium;
   (f) positioning a first epicardial lead near said neurovascular bundle of the latissimus dorsi;
   (g) positioning a second epicardial lead near said locus;
   (h) completing surgery and allowing postoperative healing for at least one week;
   (i) electrically stimulating the latissimus dorsi over a period of three weeks; and
   (j) subsequently effecting continuous pacing with the muscle pacer R-wave adjusted to be synchronous with the QRS of the patient's cardiogram.

* * * * *